(12) United States Patent
Moffitt et al.

(10) Patent No.: US 8,260,424 B2
(45) Date of Patent: Sep. 4, 2012

(54) SYSTEMS AND METHODS FOR DETECTING A LOSS OF ELECTRICAL CONNECTIVITY BETWEEN COMPONENTS OF IMPLANTABLE MEDICAL LEAD SYSTEMS

(75) Inventors: Michael A. Moffitt, Valencia, CA (US); Christopher B. Gould, Valencia, CA (US); Daniel Aghassian, Los Angeles, CA (US); Marco Henry Gin, Northridge, CA (US); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 870 days.

(21) Appl. No.: 12/258,324

(22) Filed: Oct. 24, 2008

(65) Prior Publication Data
US 2010/0106204 A1    Apr. 29, 2010

(51) Int. Cl.
*A61N 1/08* (2006.01)
(52) U.S. Cl. ............................................ 607/37; 607/38
(58) Field of Classification Search ............... 607/37–38
See application file for complete search history.

(56) References Cited

U.S. PATENT DOCUMENTS

| | | | |
|---|---|---|---|
| 4,172,459 A | 10/1979 | Hepp | |
| 4,962,766 A | 10/1990 | Herzon | |
| 5,179,952 A | 1/1993 | Buinevicius et al. | |
| 5,433,739 A | 7/1995 | Sluijter et al. | |
| 5,614,887 A | 3/1997 | Buchbinder | |
| 5,684,460 A | 11/1997 | Scanlon | |
| 5,713,935 A | 2/1998 | Prutchi et al. | |
| 5,720,771 A | 2/1998 | Snell | |
| 6,167,303 A | 12/2000 | Thompson | |
| 6,167,312 A | 12/2000 | Goedeke | |
| 6,181,969 B1 | 1/2001 | Gord | |
| 6,208,897 B1 | 3/2001 | Jorgenson et al. | |
| 6,266,564 B1 | 7/2001 | Hill et al. | |
| 6,317,633 B1 | 11/2001 | Jorgenson et al. | |

(Continued)

FOREIGN PATENT DOCUMENTS
WO    0218009 A1    3/2002
(Continued)

OTHER PUBLICATIONS

U.S. Appl. No. 11/238,240, filed Sep. 29, 2005.
(Continued)

*Primary Examiner* — Scott Getzow
*Assistant Examiner* — Hiba El-Kaissi
(74) *Attorney, Agent, or Firm* — Frommer Lawrence & Haug LLP; Patrick R. Turner

(57) ABSTRACT

A connection monitoring system for an implantable medical lead system includes an implantable lead, a first trial system cable, an external trial system, and a sensor. The lead has a distal end and at least one proximal end. The lead includes a plurality of terminals disposed at each proximal end. The first trial system cable has a distal end and at least one proximal end. The distal end of the first trial system cable is configured and arranged to electrically couple with the lead. The external trial system is configured and arranged to electrically couple with the first trial system cable. The sensor is electrically coupled to the external trial system. The sensor is configured and arranged for detecting a loss of electrical connectivity between the external trial system and the lead when the lead becomes electrically decoupled from the external trial system.

23 Claims, 13 Drawing Sheets

U.S. PATENT DOCUMENTS

| | | |
|---|---|---|
| 6,447,448 B1 | 9/2002 | Ishikawa et al. |
| 6,496,734 B1 | 12/2002 | Money et al. |
| 6,516,227 B1 | 2/2003 | Meadows et al. |
| 6,549,807 B1 | 4/2003 | Kroll |
| 6,553,256 B1 | 4/2003 | Jorgenson et al. |
| 6,564,104 B2 | 5/2003 | Nelson et al. |
| 6,609,029 B1 | 8/2003 | Mann et al. |
| 6,609,032 B1 | 8/2003 | Woods et al. |
| 6,687,538 B1 | 2/2004 | Hrdlicka |
| 6,735,479 B2 | 5/2004 | Fabian et al. |
| 6,741,892 B1 | 5/2004 | Meadows et al. |
| 6,807,965 B1 | 10/2004 | Hickle |
| 6,853,861 B1 | 2/2005 | Obel et al. |
| 6,944,500 B1 | 9/2005 | Hedberg et al. |
| 7,155,283 B2 | 12/2006 | Ries et al. |
| 7,216,001 B2 | 5/2007 | Hacker et al. |
| 7,231,253 B2 | 6/2007 | Tidemand et al. |
| 7,239,920 B1 | 7/2007 | Thacker et al. |
| 7,244,150 B1 | 7/2007 | Brase et al. |
| 7,313,529 B2 | 12/2007 | Thompson |
| 7,321,793 B2 | 1/2008 | Ben Ezra et al. |
| 7,359,751 B1* | 4/2008 | Erickson et al. ............ 607/27 |
| 7,389,142 B2 | 6/2008 | Holmstrom et al. |
| 7,437,192 B2 | 10/2008 | Gill et al. |
| 7,437,193 B2 | 10/2008 | Parramon |
| 2002/0120307 A1* | 8/2002 | Jorgenson et al. ............ 607/27 |
| 2003/0097167 A1 | 5/2003 | Friedman |
| 2003/0114905 A1 | 6/2003 | Kuzma |
| 2004/0059392 A1 | 3/2004 | Parramon et al. |
| 2004/0127954 A1 | 7/2004 | McDonald |
| 2004/0193068 A1 | 9/2004 | Burton et al. |
| 2004/0260355 A1* | 12/2004 | Holleman et al. ............ 607/37 |
| 2005/0131483 A1 | 6/2005 | Zhao et al. |
| 2005/0165323 A1 | 7/2005 | Montgomery et al. |
| 2005/0165465 A1 | 7/2005 | Pianca et al. |
| 2005/0177194 A1 | 8/2005 | Bjorling |
| 2006/0052833 A1 | 3/2006 | Legay et al. |
| 2006/0135877 A1 | 6/2006 | Giftakis et al. |
| 2006/0155207 A1 | 7/2006 | Lynn et al. |
| 2006/0247706 A1 | 11/2006 | Germanson et al. |
| 2007/0011399 A1 | 1/2007 | Dahman et al. |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0219595 A1 | 9/2007 | He |
| 2007/0239243 A1 | 10/2007 | Moffitt et al. |
| 2007/0255352 A1 | 11/2007 | Roline et al. |
| 2008/0065158 A1 | 3/2008 | Ben-Ezra et al. |
| 2008/0071320 A1 | 3/2008 | Brase |
| 2008/0208290 A1 | 8/2008 | Phillips et al. |
| 2008/0262582 A1* | 10/2008 | Alexander et al. ............ 607/116 |
| 2009/0005830 A1 | 1/2009 | Zhu et al. |

FOREIGN PATENT DOCUMENTS

| | | |
|---|---|---|
| WO | WO-02/18009 A1 | 3/2002 |
| WO | WO-03/051175 A2 | 6/2003 |
| WO | WO-2004/064632 A1 | 8/2004 |
| WO | 2006119131 A1 | 11/2006 |
| WO | 2008088569 A1 | 7/2008 |
| WO | WO-2009/006327 A1 | 1/2009 |
| WO | WO-2009/006339 A1 | 1/2009 |

OTHER PUBLICATIONS

Official Communication, U.S. Appl. No. 12/494,043, mailed Dec. 6, 2011.

Official Communication, U.S. Appl. No. 12/494,043, mailed Aug. 19, 2011.

* cited by examiner

SYSTEMS AND METHODS FOR DETECTING A LOSS OF ELECTRICAL CONNECTIVITY BETWEEN COMPONENTS OF IMPLANTABLE MEDICAL LEAD SYSTEMS

TECHNICAL FIELD

The present invention is directed to the area of implantable medical lead systems and methods of making and using the systems. The present invention is also directed to implantable medical lead systems that include a connection monitoring system for detecting a loss of electrical connectivity between two or more components of the implantable medical lead system, as well as methods of making and using the implantable medical lead systems.

BACKGROUND

Implantable medical lead systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, medical lead systems can be implanted subcutaneously to stimulate subcutaneous tissue including subcutaneous nerves such as the occipital nerve.

Implantable medical lead systems have been developed to provide therapy for a variety of treatments. An implantable medical lead system can include a control module (with a pulse generator or a receiver or both), one or more leads, and an array of electrodes on each lead. The electrodes are in contact with or near the nerves, muscles, or other tissue to be stimulated or recorded or both. The pulse generator in the control module generates electrical pulses that are delivered by the electrodes to body tissue. The receiver in the control module receives electrical activity that is recorded by the electrodes from body tissue.

BRIEF SUMMARY

In one embodiment, a connection monitoring system for an implantable medical lead system includes an implantable lead, a first trial system cable, an external trial system, and a sensor. The lead has a distal end and at least one proximal end. The lead includes a plurality of terminals disposed at each proximal end. The first trial system cable has a distal end and at least one proximal end. The distal end of the first trial system cable is configured and arranged to electrically couple with the lead. The external trial system is configured and arranged to electrically couple with the first trial system cable. The sensor is electrically coupled to the external trial system. The sensor is configured and arranged for detecting a loss of electrical connectivity between the external trial system and the lead when the lead becomes electrically decoupled from the external trial system.

In another embodiment, a connection monitoring system for an implantable medical lead system includes an implantable lead, a lead extension, a control module, and a sensor. The implantable lead has a distal end and at least one proximal end. The lead includes a plurality of terminals disposed at each proximal end. The lead extension has a distal end and at least one proximal end. The distal end of the lead extension is configured and arranged to electrically couple with the lead. The control module is configured and arranged to electrically couple with the lead extension. The sensor is electrically coupled to the external trial system. The sensor is configured and arranged for detecting a loss of electrical connectivity between the control module and the lead when the lead becomes electrically decoupled from the control module.

In yet another embodiment, a method for monitoring an implantable medical lead system for a loss of electrical connectivity includes implanting a distal end of a lead into a patient so that a proximal end of the lead extends from the patient. The distal end of the lead includes a plurality of electrodes. The proximal end of the lead includes a plurality of terminals. The proximal end of the lead is electrically coupled to a connector disposed at a distal end of a first trial system cable so that at least one of the terminals electrically couples to a pair of conductor pins disposed in the connector to one another. Each conductor pin of the pair of conductor pins is electrically coupled to a sensor disposed in an external trial system. Impedance values within at least one predetermined range are monitored between the two conductor pins of the trial system cable. An indication is provided when the sensor detects impedance values within one of the predetermined ranges.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable medical lead systems and methods of making and using the systems. The present invention is also directed to implantable medical lead systems that include a connection monitoring system for detecting a loss of electrical connectivity between two or more components of the implantable medical lead system, as well as methods of making and using the implantable medical lead systems.

An implantable medical lead system may include an implantable electrical recording system or an implantable electrical stimulation system. For clarity, embodiments are discussed with reference to implantable electrical stimulation systems. However, it will be understood that embodiments including implantable electrical recording systems are equally applicable.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
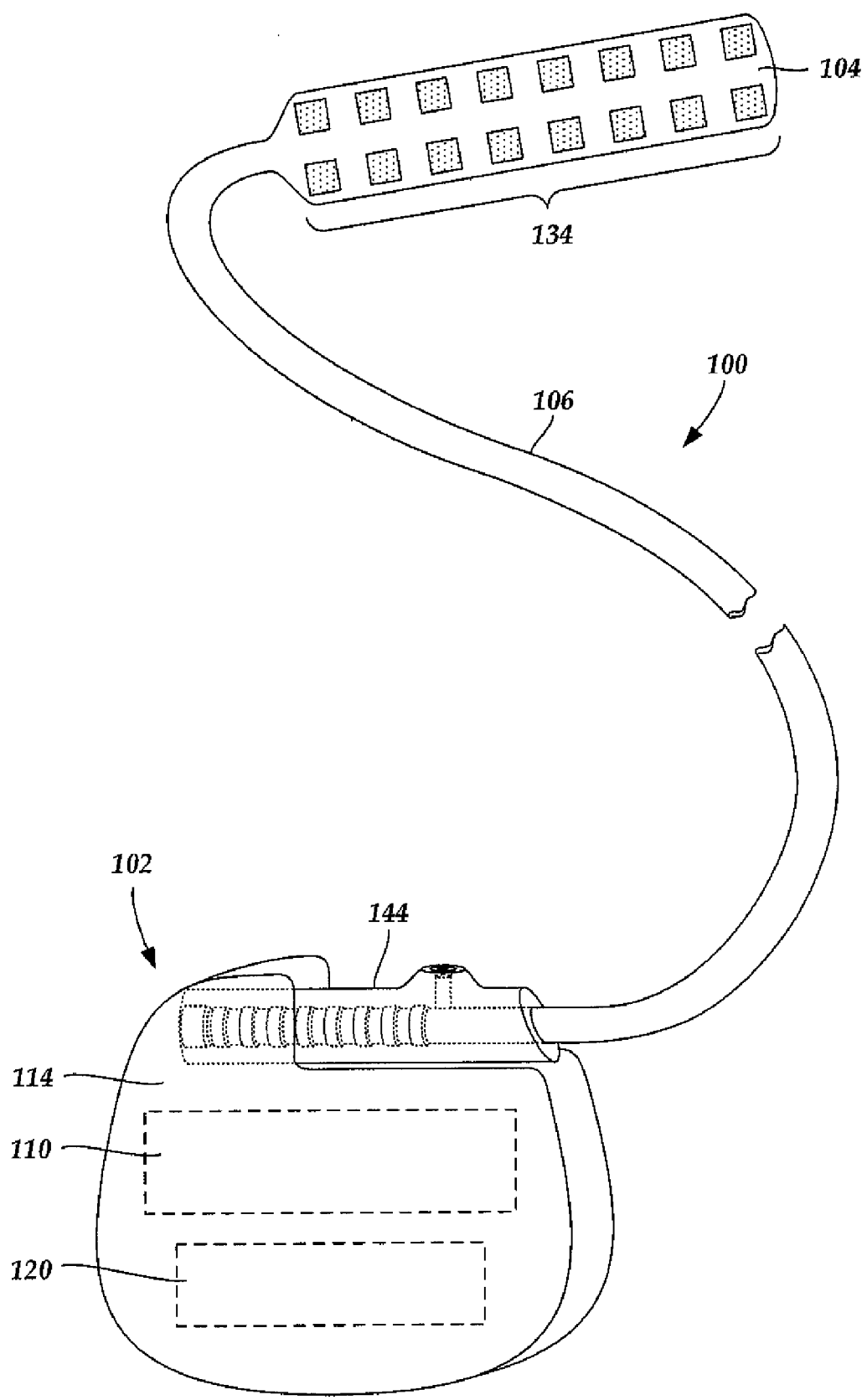
FIG. 1 is a schematic view of one embodiment of an electrical stimulation system, according to the invention.
Figure 2:
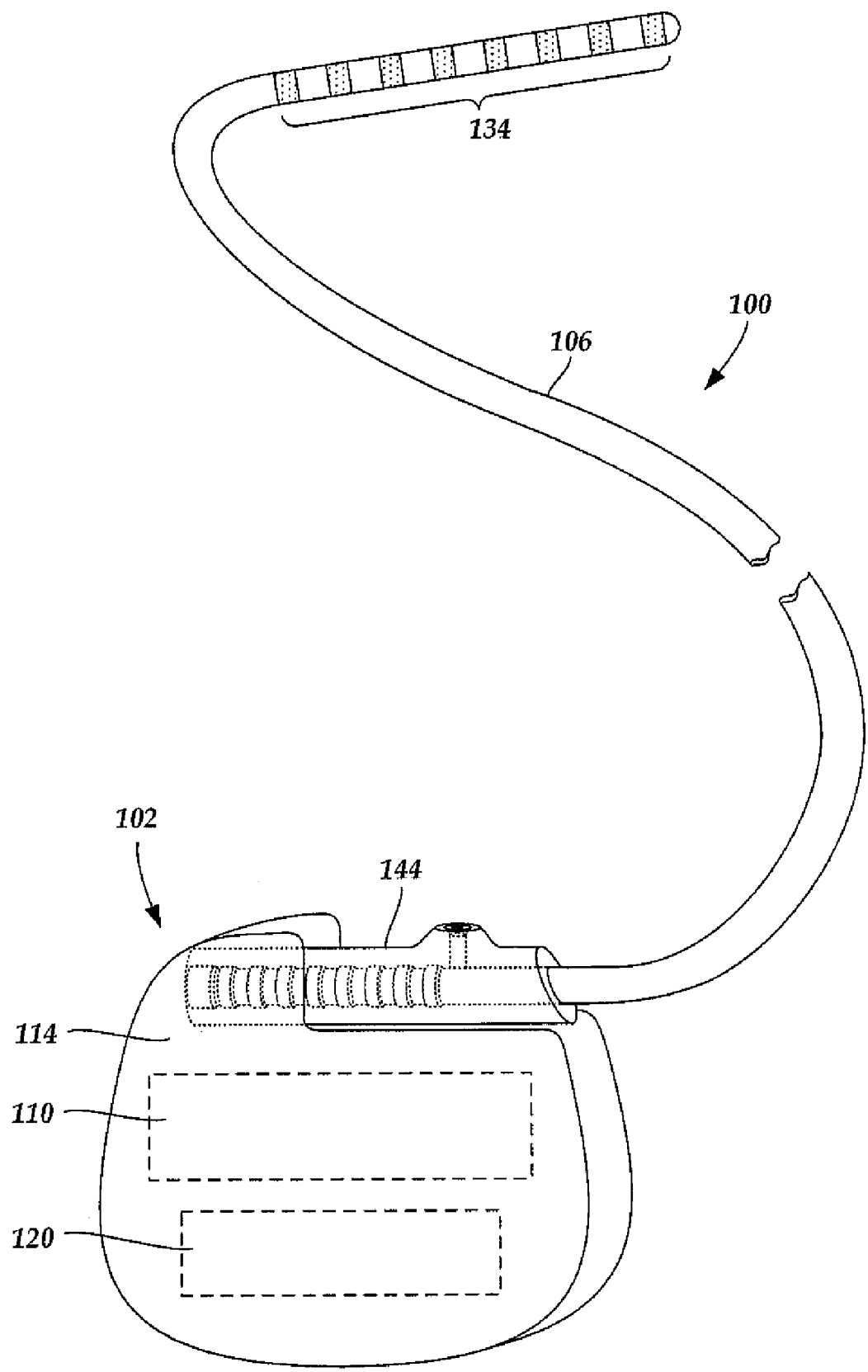
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 324 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a nonconductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, a trial system cable, or an adaptor). Conductors (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. There may also be one or more lumens (not shown) that open at, or near, the proximal end of the lead, for example, for inserting a stylet rod to facilitate placement of the lead within a body of a patient.

Implantable electrical recording systems may include leads that are structurally similar to leads of an implantable electrical stimulation system. However, with implantable electrical recording systems, electrodes record electrical activity and a receiver in the control module receives the recorded electrical activity. Processing of the received electrical activity may be performed by a processor in the control module, or by an external processor, or both. In at least some embodiments, implantable medical lead systems may include both recording and stimulation functionality.

Figure 3A:
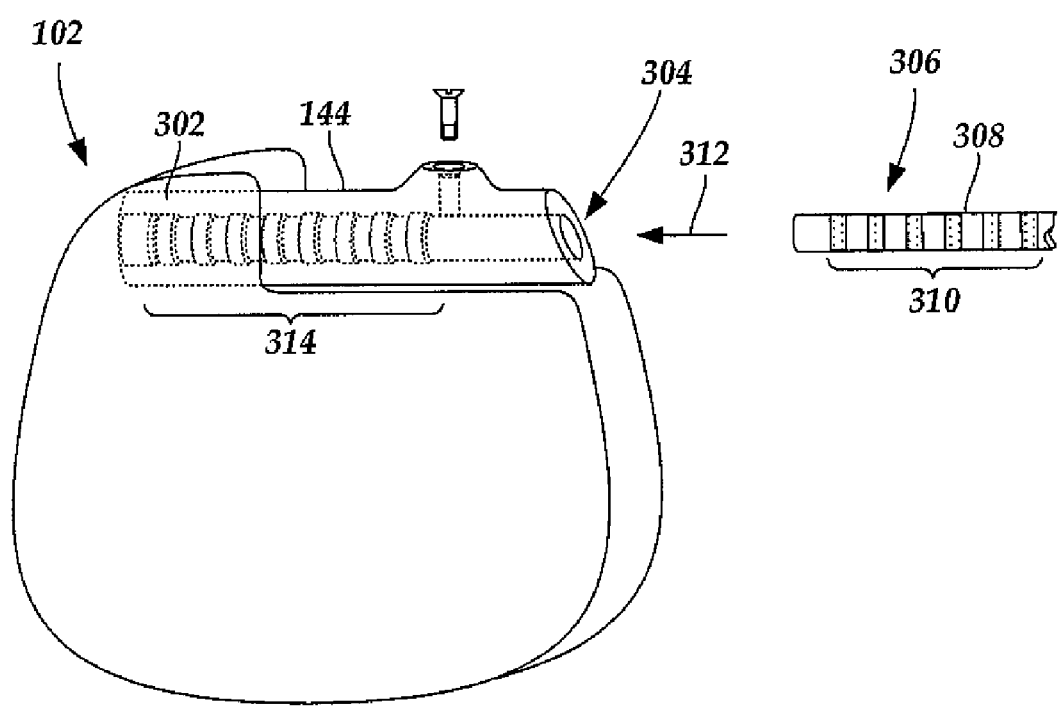
FIG. 3A is a schematic view of one embodiment of a proximal portion of a lead and a control module of an implantable medical lead system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
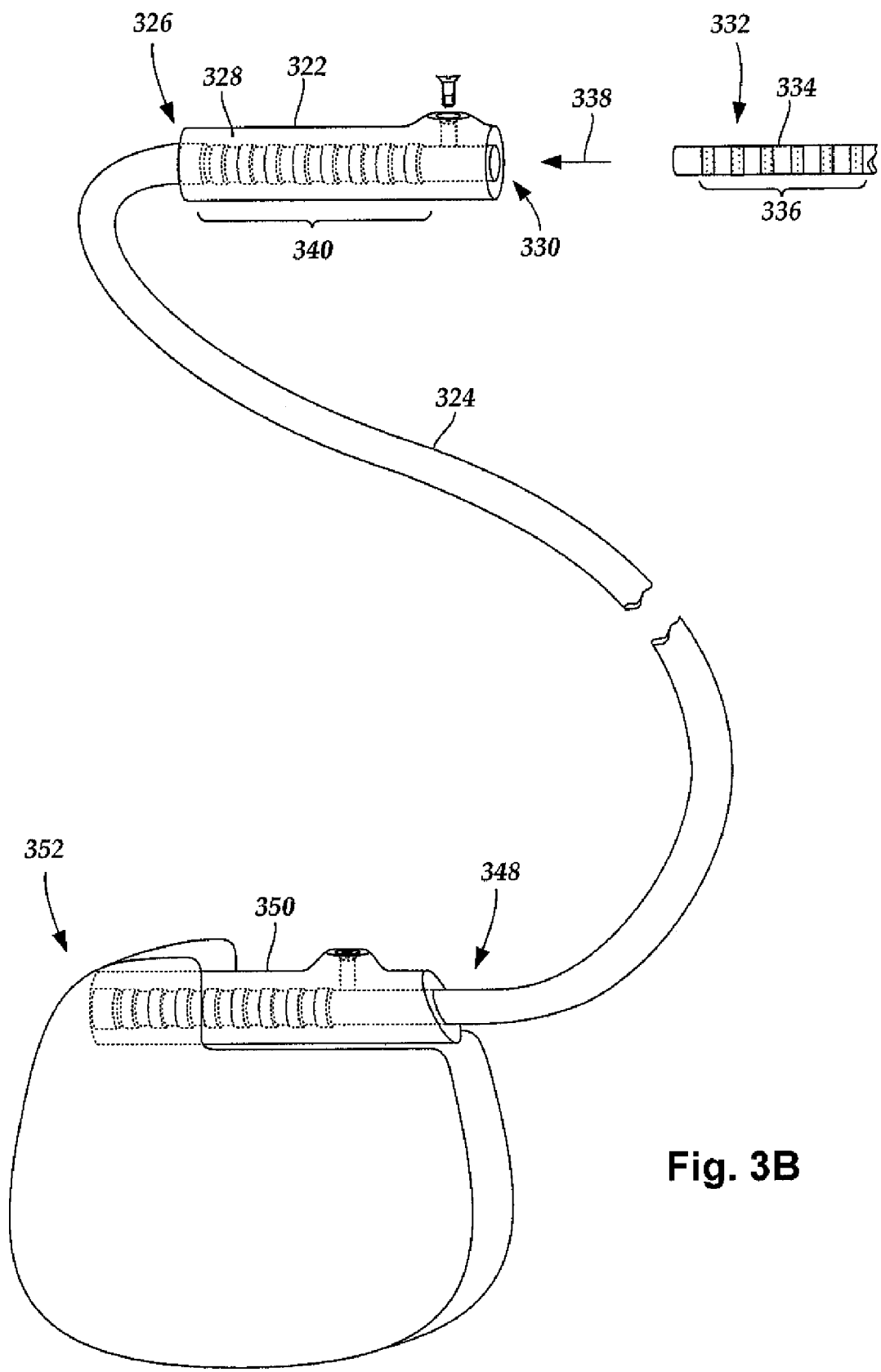
FIG. 3B is a schematic view of one embodiment of a proximal portion of a lead and a lead extension of an implantable medical lead system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

Sometimes a trial stimulation is performed on a patient before an implantable medical lead system is completely implanted in the patient. During the trial stimulation, the patient's response to a variety of stimulation parameters may be analyzed over a period of time prior to complete implantation of the implantable medical lead system into the patient. A trial stimulation may last for several days, or even one or more weeks. During a trial stimulation, a patient is typically able to make adjustments to received stimulation. For example, a patient may be able to turn the stimulation on and off, or adjust one or more stimulation parameters, such as stimulation amplitude, or switch between two or more different pre-programmed stimulation patterns, as desired. In at least some embodiments, a patient may be able to make stimulation adjustments using a remote control.

During a trial stimulation, a distal end of a lead (or an entire lead and a distal end of a lead extension) is implanted into the patient at a selected location, while a proximal end of the lead (or lead extension) is electrically coupled to an external trial system via a trial system cable (and, optionally, one or more trial system cable extensions). It will be understood that a trial recording may also be performed instead of, or in addition to, a trial stimulation.

Figure 4A:
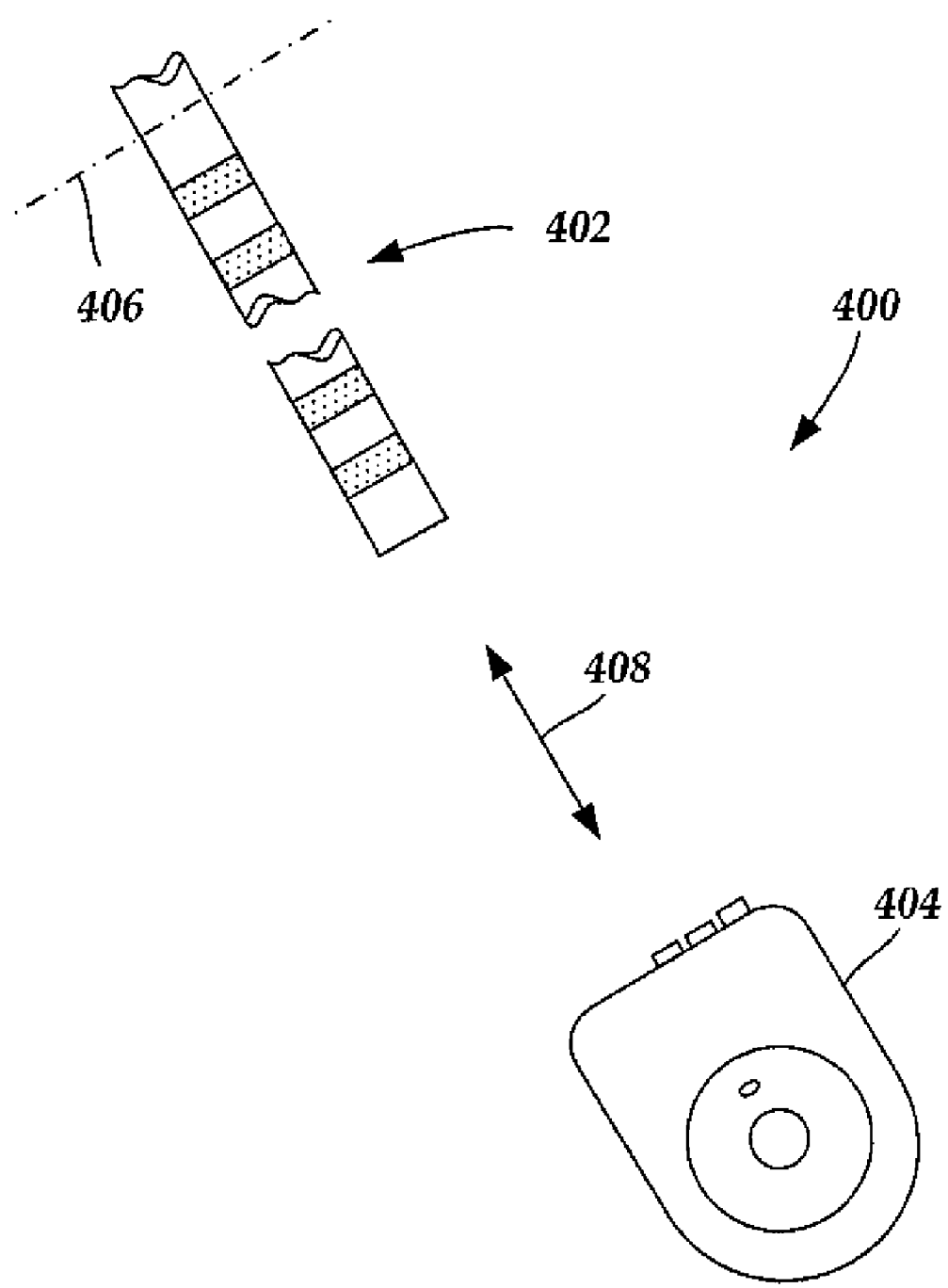
FIG. 4A is a schematic exploded view of one embodiment of an implantable medical lead system suitable for a trial stimulation, the implantable medical lead system including a proximal portion of a lead (or lead extension) configured and arranged to electrically couple to an external trial system.

FIG. 4A is a schematic view of one embodiment of an implantable medical lead system 400 suitable for using to perform a trial stimulation on a patient. The implantable medical lead system 400 includes a lead 402 and an external trial system 404. In at least some embodiments, a distal end of the lead 402 is implanted into a patient so that a proximal end of the lead 402 remains external to the patient, as shown by a line 406 of alternating dashes and dots representing the internal/external interface of the patient. The proximal end of the lead 402 may be electrically coupled directly with the external trial system, as shown by two-headed arrow 408.

In at least some alternate embodiments, the lead 402 may be entirely implanted into the patient and electrically coupled to a distal end of a lead extension with a proximal end that remains external to the patient. Accordingly, in at least some embodiments the proximal end of the lead extension may be electrically coupled to the external trial system 404. In at least some embodiments, an implantable medical lead system may also include other intermediate conductors, such as one or more additional lead extensions.

Figure 4B:
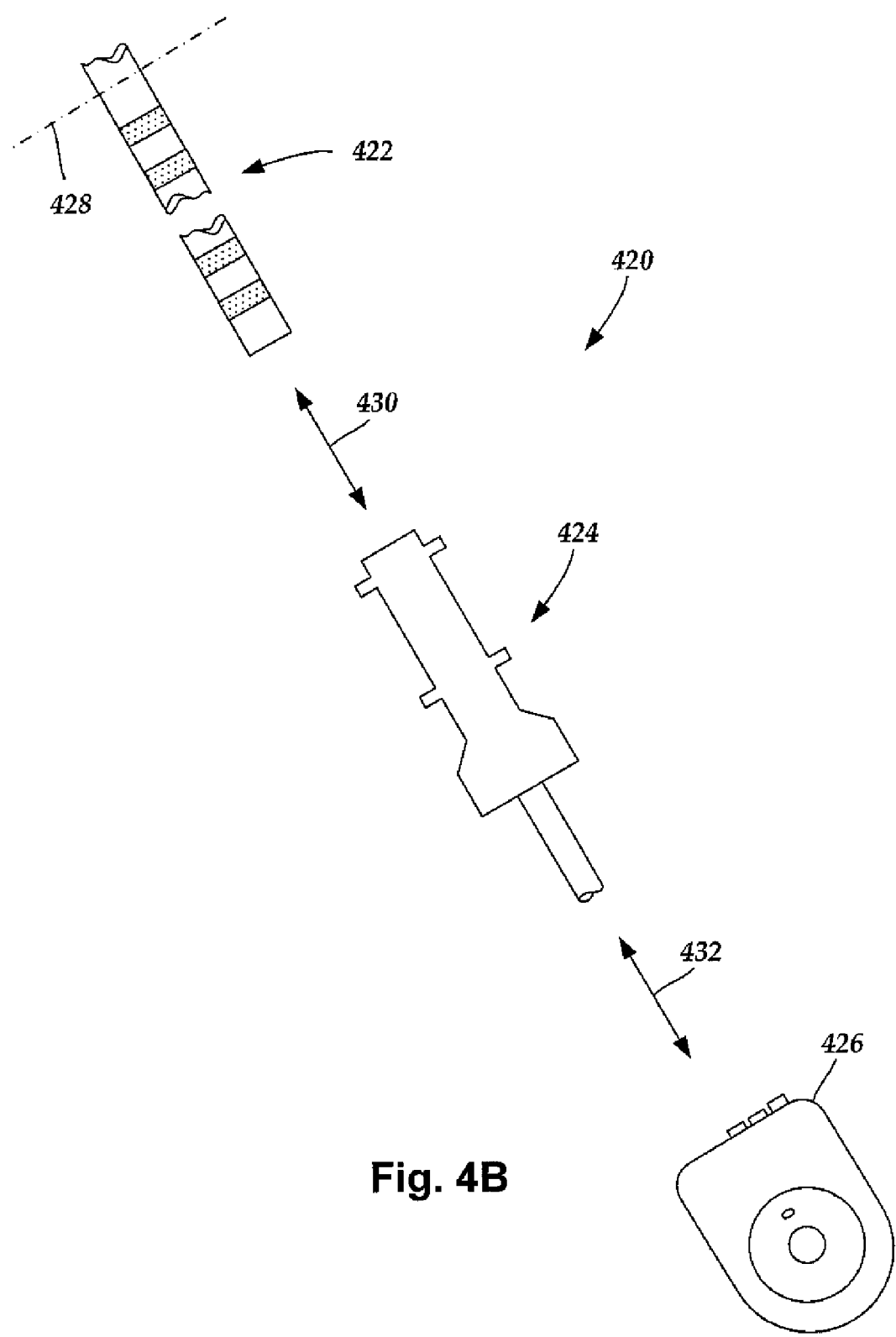
FIG. 4B is a schematic exploded view of one embodiment of an implantable medical lead system suitable for a trial stimulation, the implantable medical lead system including a proximal portion of a lead (or lead extension) configured and arranged to electrically couple to a trial system cable which, in turn, is configured and arranged to electrically couple to an external trial system.

FIG. 4B is a schematic view of another embodiment of an implantable medical lead system 420 suitable for using to perform a trial stimulation on a patient. The implantable medical lead system 420 includes a lead 422, a trial system cable 424, and an external trial system 426. In at least some embodiments, a distal end of the lead 422 is implanted into a patient so that a proximal end of the lead 422 remains external to the patient, as shown by a line 428 of alternating dashes and dots representing the internal/external interface of the patient. The proximal end of the lead 422 may be electrically coupled to a distal end of the trial system cable 424, as shown by two-headed arrow 430. A proximal end of the trial system cable 424 may, in turn, be electrically coupled to the external trial system 426, as shown by two-headed arrow 432.

In at least some alternate embodiments, the lead 422 may be entirely implanted into the patient and electrically coupled to a distal end of a lead extension with a proximal end that remains external to the patient. Accordingly, in at least some embodiments the proximal end of the lead extension may be electrically coupled to the external trial system 426 via the trial system cable 424. In at least some embodiments, an implantable medical lead system may also include other intermediate conductors, such as one or more additional lead extensions.

In at least some embodiments, an implantable medical lead system 420 may include one or more trial system cable extensions. In at least some embodiments, a proximal end of the trial system cable 424 may be electrically coupled to a distal end of a trial system cable extension. In at least some embodiments, a proximal end of the trial system cable extension may, in turn, be electrically coupled to the external trial system 426. In at least some embodiments, the trial system cable 424 may be configured and arranged to receive a plurality of leads or lead extensions.

Electrical connectivity between the lead and the external trial system may, on occasion, become lost. It may be the case that a patient does not immediately notice that electrical connectivity is lost and may, instead, attribute a loss of therapeutic affect to a sub-therapeutic setting on the external trial system. Consequently, the patient may increase one or more of the stimulation parameters. Sometimes the patient may subsequently reconnect the disconnection without first lowering the increased stimulation parameters and accidently overstimulate him or herself. Electrical connectivity may also become lost between a lead and a control module at some point subsequent to implantation of the control module.

An electrical-connectivity monitoring system ("connection monitoring system") for an implantable medical lead system is described. In some embodiments, the connection monitoring system detects losses of electrical connectivity in an implantable medical lead system occurring somewhere along a conductive path between a lead and an external trial system during a trial stimulation. In other embodiments, the connection monitoring system detects losses of electrical connectivity in an implantable medical lead system occurring somewhere along a conductive path between a lead and a control module subsequent to implantation. In at least some embodiments, the connection monitoring system may also be able to distinguish between different types of trial system cables (e.g., a trial system cable with one proximal end and sixteen conductors for electrically coupling with sixteen electrodes on a connected lead, or a trial system cable with two proximal ends and eight conductors on each proximal end, each conductor coupling with eight electrodes on a connected lead), or one or more other accessory devices, such as a test load box, connector box, or the like.

The loss of connectivity may occur within one or more of the components, such as a lead, lead extension, trial system cable, trial system cable extension, or external trial system. However, in practice it is more likely that the loss of connectivity happens due to one or more disconnections between components. For example, in at least some embodiments, the loss of connectivity may occur between a lead (or lead extension) and a trial system cable. In at least some embodiments, the loss of connectivity may occur between the trial system cable and the trial system cable extension. In at least some embodiments, the loss of connectivity may occur between two trial system cable extensions. In at least some embodiments, the loss of connectivity may occur between the trial system cable (or trial system cable extension) and the external trial system. In at least some embodiments, the loss of connectivity may occur between the lead and the lead extension. In at least some embodiments, the loss of connectivity may occur between the lead (or lead extension) and the control module.

In the case of external trial systems with multiple ports, in addition to a loss of connectivity occurring, trial system cables (and trial system cable extensions) may be inserted into the incorrect port. Insertion of a trial system cable (or a trial system cable extension) into the incorrect port of an external trial system may result in undesired stimulation of a patient.

Figure 5A:
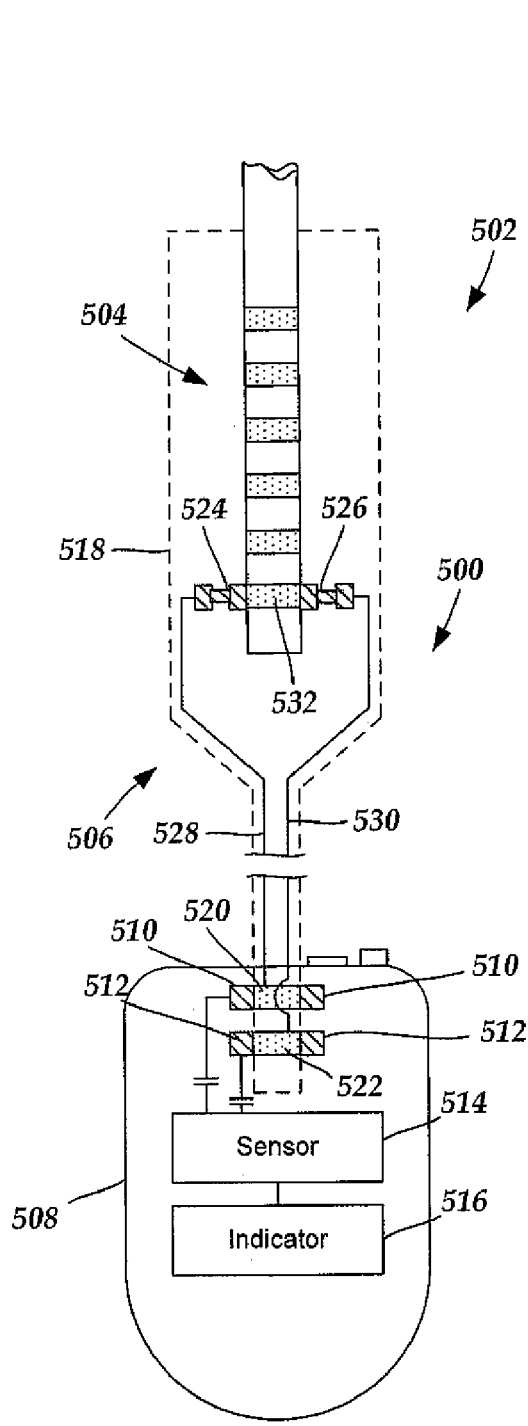
FIG. 5A is a schematic view of one embodiment of a connection monitoring system for an implantable medical lead system, the connection monitoring system including an external trial system with a sensor and an indicator, the sensor configured and arranged for detecting a loss of electrical connectivity between a proximal end of a lead and the external trial system, the indicator configured and arranged for signaling the loss of electrical connectivity, according to the invention.

FIG. 5A is a schematic view of one embodiment of a connection monitoring system 500 for an implantable medical lead system 502. The connection monitoring system 500 includes a lead (or lead extension) 504 electrically coupled to a trial system cable 506 which, in turn, is electrically coupled to an external trial system 508. The external trial system 508 includes two conductor pins 510 and 512, a sensor 514 electrically coupled to each of the two conductor pins 510 and 512, and an indicator 516 electrically coupled to the sensor 514. In at least some embodiments, the two conductor pins 510 and 512 are disposed in a connector disposed on the external trial system 508. In FIG. 5A, and in some subsequent figures, the conductor pins are shown as two cross-hatched boxes connected to one another by a smaller cross-hatched box (see e.g., conductor pins 524 and 526), representing an end view of a conductor pin that is U-shaped or C-shaped. It will be understood that many other shapes of conductor pins are possible.

The trial system cable 506 includes a connector 518 at a distal end and connective contacts 520 and 522 at a proximal end. The connector 518 includes two conductor pins 524 and 526. Each of the conductor pins 524 and 526 is electrically coupled to the connective contacts 520 and 522, respectively, disposed at a proximal end of the trial system cable 506, via conductors 528 and 530, respectively. The lead (or lead extension) 504 includes at least one terminal 532. It will be understood that additional conductor pins disposed in the connector 518 (and in the external trial system 508) are omitted for clarity of illustration. Additionally, it will be understood that additional connective contacts disposed on the proximal end of the trial system cable 506 are also omitted in FIG. 5A for clarity of illustration. Furthermore, it will be understood that each of the conductor pins (e.g., conductor pins 510 and 512) disposed on the external trial system 508 may or may not be coupled to a current/voltage source (not shown in FIG. 5). Moreover, it will be understood that additional conductors may also be employed to electrically couple the additional conductor pins to additional connective contacts on the trial system cable (or trial system cable extension) and to various electrical components within the external trial system 508 (e.g., the sensor 514, one or more current sources, and the like).

In at least some embodiments, the sensor 514 either periodically or continually detects the impedance, current, voltage difference, or the like, between the conductor pins 510 and 512. In at least some embodiments, when the lead (or lead extension) 504 is fully inserted into the connector 518 of the trial system cable 506, the terminal 532 disposed on the lead (or lead extension) 504 electrically couples the two conductor pin 524 and 526 to one another to produce a relatively low impedance path. Additionally, in at least some embodiments, when the trial system cable 506 is fully inserted into the external trial system 508, the connective contacts 520 and 522 disposed in the trial system cable 506 electrically couple to the conductive pins 510 and 512, respectively, of the external trial system 508.

Thus, in at least some embodiments, when the lead (or lead extension) 504 is fully inserted into the trial system cable 506 and the trial system cable 506 is fully inserted into the external trial system 508, the sensor 514 senses that the impedance between the conductor pins 510 and 512 is below a threshold value indicating that the lead (or lead extension) 504 is electrically coupled to the external trial system 508. Conversely, in at least some embodiments, when either or both the lead (or lead extension) 504 is not fully inserted into the trial system cable 506 or the trial system cable 506 is not fully inserted into the external trial system 508, the sensor 514 senses that the impedance between the conductor pins 510 and 512 is above a threshold impedance value indicating that the lead (or lead extension) 504 is not electrically coupled to the external trial system 508 and, accordingly, electrical connectivity is lost between the lead 504 and the external trial system 508.

In at least some embodiments, when a loss of electrical connectivity is detected, one or more signals may be emitted. Many different types of signals may be emitted from the indicator 516 including, for example, at least one auditory signal, at least one visual signal, at least one tactile signal, at least one olfactory signal, a telemetry signal to another device, or the like or combinations thereof. For example, an emitted signal may include one or more beeps, chirps, squeaks, chimes, rings, the activation or de-activation of one or more lights or light-emitting diodes one or more times, a message may be displayed on one or more displays, one or more vibrations or tactile pulses, the emission of one or more peculiar odors, and the like or combinations thereof. In at least some embodiments, the indicator 516 is disposed on the external trial system 508. In at least some embodiments, the indicator 516 is disposed on a remote control (not shown in FIG. 5A). In at least some embodiments, the external trial system 508 and the remote control include the indicator 516. In at least some embodiments, the indicator 516 is disposed on an electronic device other than the external trial system 508 or the remote control. In at least some embodiments, the connection monitoring system 500 shown in FIG. 5A may be implemented in a similar manner, with a lead electrically coupled to a lead extension which, in turn, is electrically coupled to a control module.

In at least some embodiments, when a loss of electrical connectivity is detected, stimulation (or recording) may be allowed to continue. In at least some embodiments, when a loss of electrical connectivity is detected, the external trial system may automatically turn off. In at least some embodiments, when a loss of electrical connectivity is detected, a message is sent via telemetry to another device (e.g., a patient remote control (which may or may not have its own indicator(s) or display a message on a screen)) either actively, or as part of a subsequent communication. In at least some embodiments, when a loss of electrical connectivity is detected, the external trial system may perform a data logging of the connect/disconnect event.

Figure 5B:
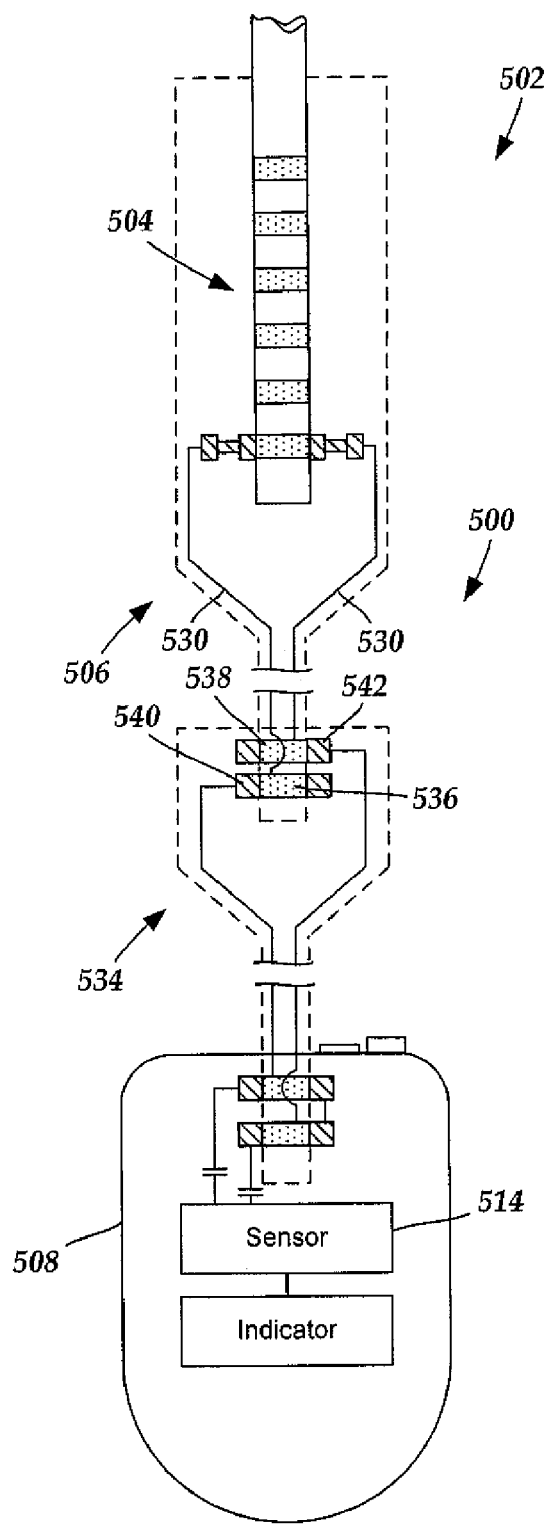
FIG. 5B is a schematic view of another embodiment of a connection monitoring system for an implantable medical lead system, the connection monitoring system including an external trial system with a sensor and an indicator, the sensor configured and arranged for detecting a loss of electrical connectivity between a proximal end of a lead and the external trial system, the indicator configured and arranged for signaling the loss of electrical connectivity, according to the invention.

In at least some embodiments, the implantable medical lead system 502 may also include one or more trial system cable extensions. FIG. 5B is a schematic view of another embodiment of a connection monitoring system 500 for an implantable medical lead system 502. The connection monitoring system 500 includes the lead (or lead extension) 504 electrically coupled to the trial system cable 506 which, in turn, is electrically coupled to a trial system cable extension 534 which, in turn, is electrically coupled to the external trial system 508. In at least some embodiments, the sensor 514 detects a loss of connectivity when one or more of: the lead (or lead extension) 504 is not fully inserted into the trial system cable 506, or the trial system cable 506 is not fully connected to the trial system cable extension 534, or the trial system cable extension 534 is not fully inserted into the external trial system 508, or when there is a loss of electrical connectivity somewhere within one or more of the above-mentioned components of the implantable medical lead system 502.

Figure 5C:
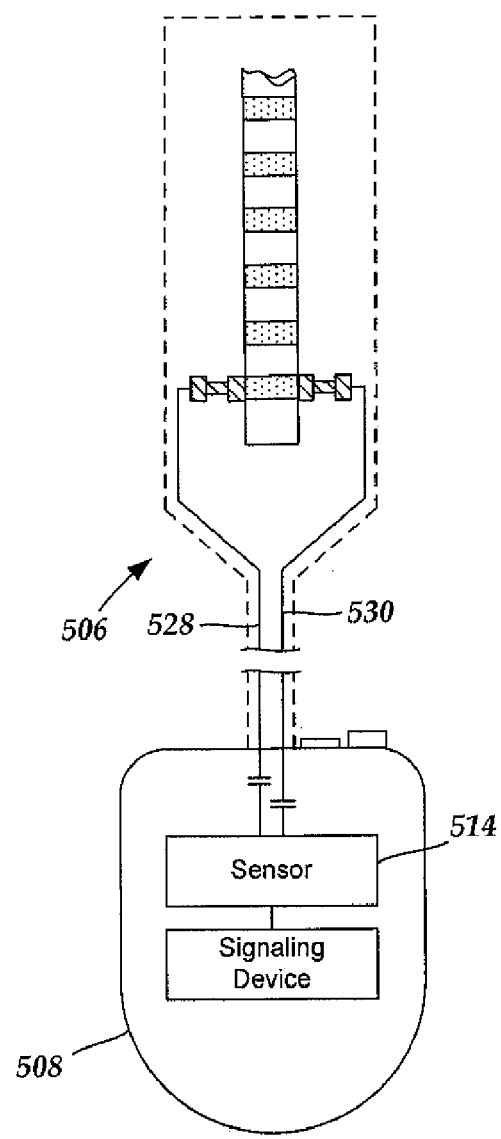
FIG. 5C is a schematic view of yet another embodiment of a connection monitoring system for an implantable medical lead system, the connection monitoring system including an external trial system with a sensor and an indicator, the sensor configured and arranged for detecting a loss of electrical connectivity between a proximal end of a lead and the external trial system, the indicator configured and arranged for signaling the loss of electrical connectivity, according to the invention.

In at least some embodiments, the trial system cable 506 is formed integrally with the external trial system 508, as shown in FIG. 5C. In at least some embodiments, when the trial system cable 506 is formed integrally with the external trial system 508, the conductors 528 and 530 may electrically couple directly with the sensor 514.

In at least some embodiments, conductor pins (e.g., 524 and 526 of FIG. 5A), may be disposed in a connector (e.g., 518 of FIG. 5A) in many different configurations so that each conductor pin aligns with a terminal of the lead (or lead extension) (e.g., 504 of FIG. 5A) when the lead (or lead extension) (e.g., 504 of FIG. 5A) is fully inserted into the connector (e.g., 518 of FIG. 5A). In some embodiments, each conductor pin is configured and arranged to electrically couple one or more electrodes disposed on a distal end of the lead to a pulse generator disposed in the external trial system 508. In some embodiments, the connection monitoring system (500 in FIG. 5A) is configured and arranged to utilize a conductor pin that is also used for providing electrical contact between the electrodes and the pulse generator. In other embodiments, a pair of conductor pins is electrically coupled to at least one of the terminals so that one of the pair of conductor pins may electrically couple one or more electrodes to the pulse generator and the other of the pair of conductor pins may be used by the connection monitoring system (500 in FIG. 5A).

Figure 6A:
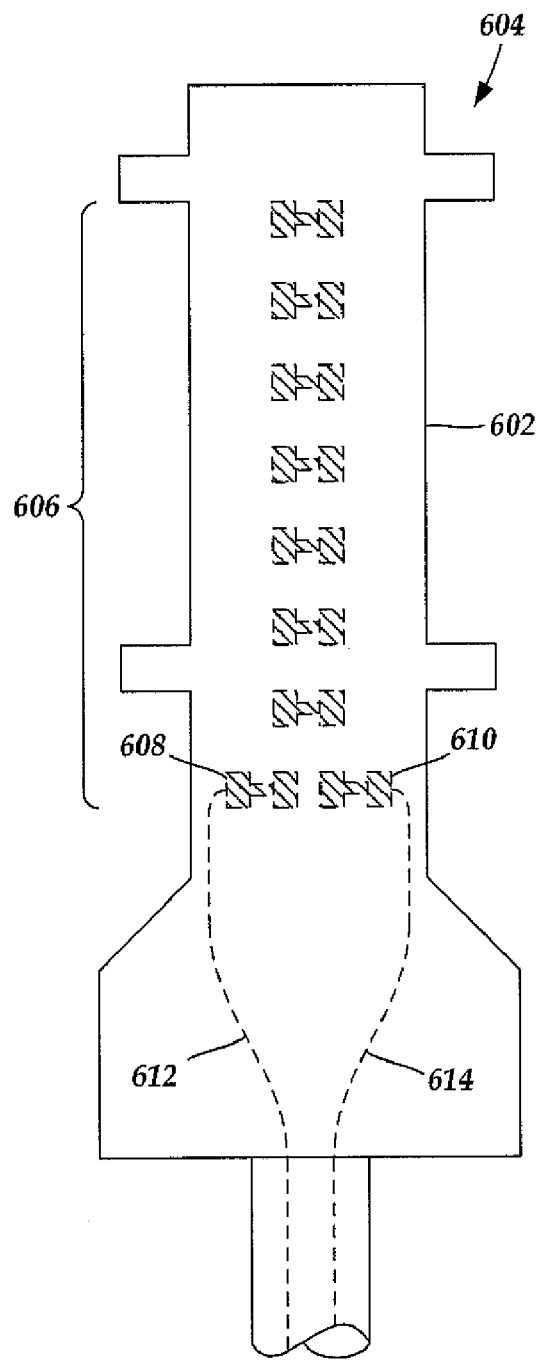
FIG. 6A is a schematic side view of one embodiment of a connector disposed on a distal end of a trial system cable, the connector including conductor pins, according to the invention.

FIG. 6A is a schematic side view of one embodiment of a connector 602 disposed on a distal end of a trial system cable 604. The connector 602 includes conductor pins 606. A pair of conductor pins 608 and 610 is laterally-spaced at a proximal-most position. Conductors 612 and 614 each extend along the length of the trial system cable 604 to electrically couple conductor pins 608 and 610, respectively, to connective contacts (e.g., 520 and 522 of FIG. 5A) disposed at a proximal end of the trial system cable 604. In FIG. 6A, the conductors 612 and 614 are electrically coupled to the proximal-most pair of conductor pins 608 and 610. In at least some embodiments, the conductors 612 and 614 are electrically coupled to other pairs of laterally-spaced conductor pins 606 disposed in the connector 602, either instead of, or in addition to, the proximal-most pair of conductor pins 608 and 610. In FIG. 6A and in subsequent figures, conductors electrically extending from the remaining conductor pins 602 have been omitted for clarity of illustration.

Figure 6B:
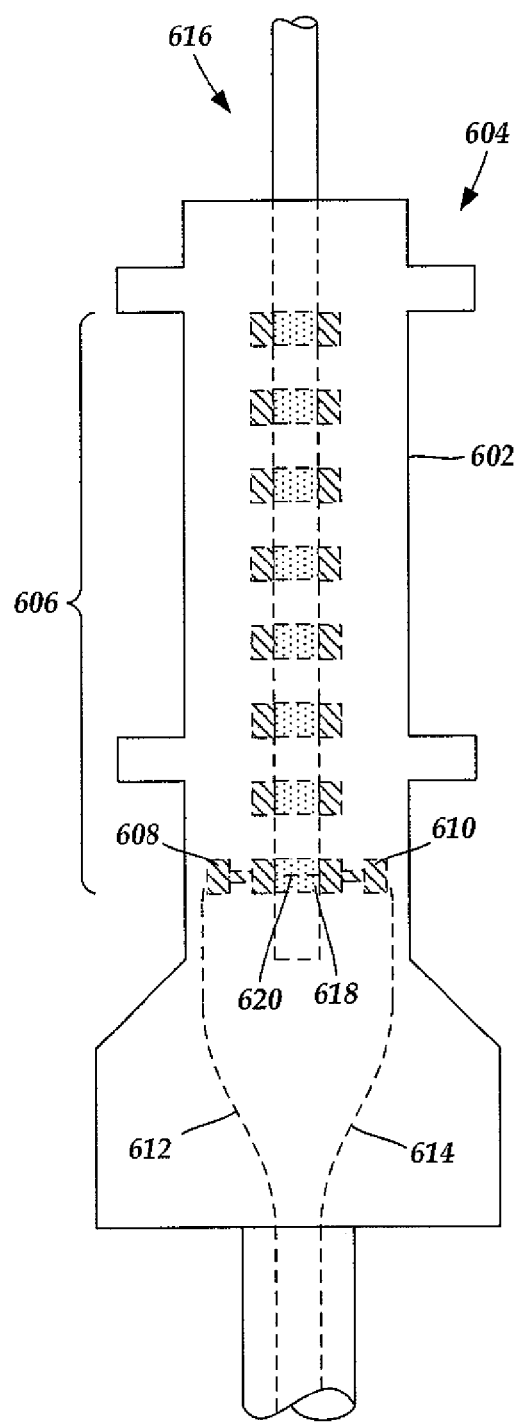
FIG. 6B is a schematic side view of one embodiment of a proximal end of a lead (or lead extension) fully inserted into a connector disposed on a distal end of the trial system cable shown in FIG. 6A, the connector including a laterally-spaced pair of conductor pins aligning with a proximal-most terminal disposed on the lead (or lead extension) to electrically couple the pair of conductor pins to one another, according to the invention.

In at least some embodiments, one or more terminals disposed on the lead (or lead extension) (see e.g., 504 in FIG. 5A) align with one or more of the conductors 606 disposed in the connector 602 to create electrical connectivity when the lead (or lead extension) (504 in FIG. 5A) is fully inserted into the connector 602. FIG. 6B is a schematic side view of one embodiment of a proximal end of a lead (or lead extension) 616 fully inserted into the connector 602. The lead (or lead extension) 616 includes a plurality of terminals, such as proximal-most terminal 618, disposed on the lead (or lead extension) 616. At least some of the terminals are configured and arranged to align with the conductor pins 606 disposed in the connector 602. In FIG. 6B, the proximal-most terminal 618 is configured and arranged to align with both of the laterally-spaced, proximal-most conductor pins 608 and 610 when the lead (or lead extension) 616 is fully inserted into the connector 602. Thus, in at least some embodiments, when the lead (or lead extension) 616 is fully inserted into the connector 602, the connection monitoring system (500 in FIG. 5A) may detect that the conductor pins 608 and 610 are electrically coupled to one another (as indicated in FIG. 6B as a dashed line 620) and consequently determine there to be electrical connectivity.

In at least some embodiments, the terminals disposed on the lead (or lead extension) 616 are configured and arranged so that, when the proximal-most terminal 618 is aligned with the proximal-most pair of conductor pins 608 and 610 (thereby establishing an indication of electrical conductivity by the connection monitoring system (500 in FIG. 5A)), the remaining terminals disposed on the lead (or lead extension) 616 also align with the remaining conductor pins 606 disposed on the connector 602. It may be an advantage to electrically couple the connection monitoring system (500 in FIG. 5A) to the proximal-most conductor pins 608 and 610. When the connection monitoring system (500 in FIG. 5A) is electrically coupled to the proximal-most conductor pins 608 and 610, a connection will not be detected if the lead (or lead extension) 616 is partially inserted such that the conductor pins 608 and 610 align with a terminal other than the proximal-most terminal 618, thereby possibly establishing spurious electrical connectivity.

Figure 6C:
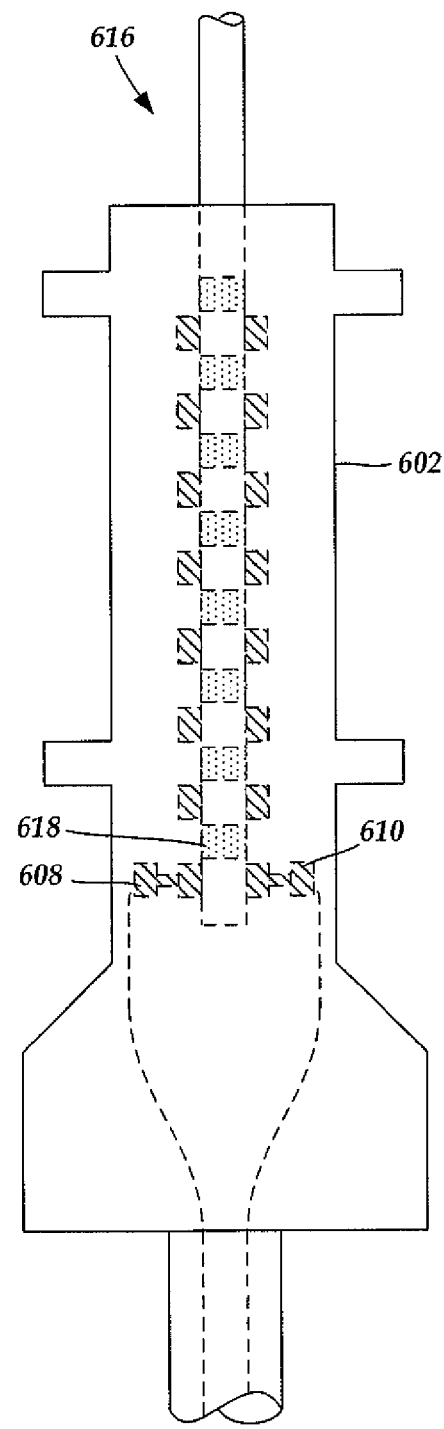
FIG. 6C is a schematic side view of one embodiment of a proximal end of the lead (or lead extension) shown in FIG. 6B partially inserted into a connector disposed on a distal end of the trial system cable shown in FIG. 6B so that a proximal-most terminal disposed on the lead (or lead extension) does not align with a pair of conductor pins disposed in the trial system cable and consequently does not electrically couple the laterally-spaced pair of conductor pins to one another, according to the invention.

FIG. 6C is a schematic side view of one embodiment of a proximal end of the lead (or lead extension) 616 partially (or improperly) inserted into the connector 602. In FIG. 6C, the lead (or lead extension) 616 is partially removed from the connector 602 so that the proximal-most terminal 618 does not align with the proximal-most conductor pins 608 and 610. Accordingly, in at least some embodiments the connection monitoring system (500 in FIG. 5A) may detect the impedance between the conductor pins (510 and 512 of FIG. 5A) to be above a threshold value to establish a loss of electrical conductivity.

Figure 7:
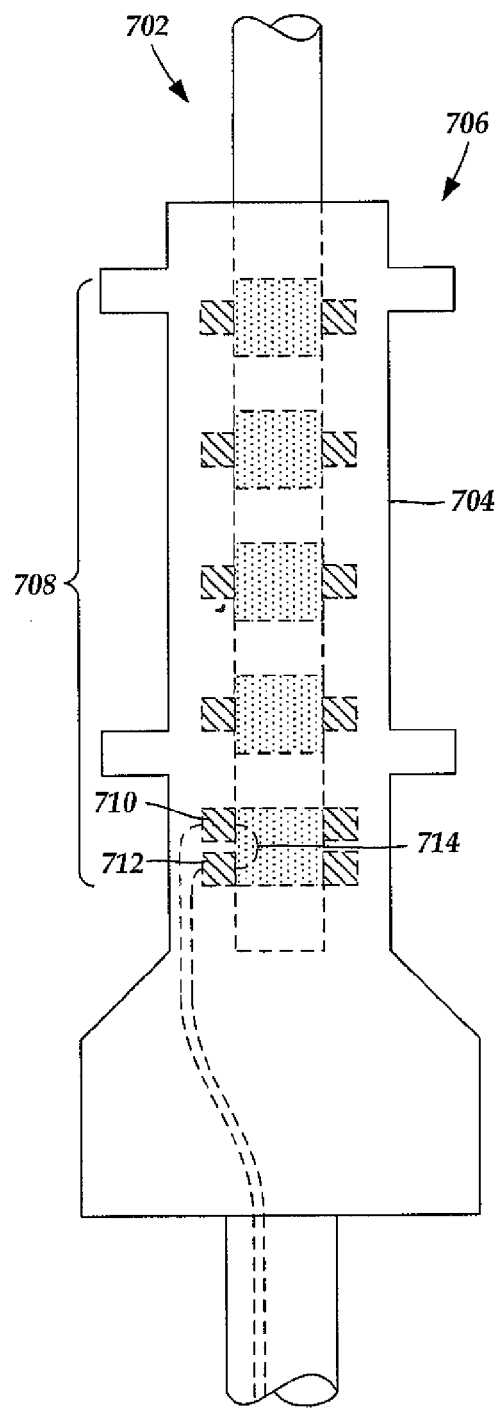
FIG. 7 is a schematic side view of one embodiment of a proximal end of a lead (or lead extension) inserted into a connector disposed on a distal end of a trial system cable, the connector including a longitudinally-spaced pair of conductor pins aligning with a proximal-most terminal disposed on the lead (or lead extension) to electrically couple the proximal-most pair of conductor pins to one another, according to the invention.

In at least some embodiments, conductor pins of the connection monitoring system (500 in FIG. 5A) may be disposed in different configurations, besides being laterally-spaced from one another. FIG. 7 is a schematic side view of one embodiment of a proximal end of a lead (or lead extension) 702 inserted into a connector 704 disposed on a distal end of a trial system cable 706. The connector 704 includes conductor pins 708. A longitudinally-spaced pair of conductor pins 710 and 712 is shown aligning with a proximal-most terminal disposed on the lead (or lead extension) 702 to electrically couple the pair of conductor pins 710 and 712 to one another, as indicated in FIG. 7 as a dashed line 714.

Figure 8:
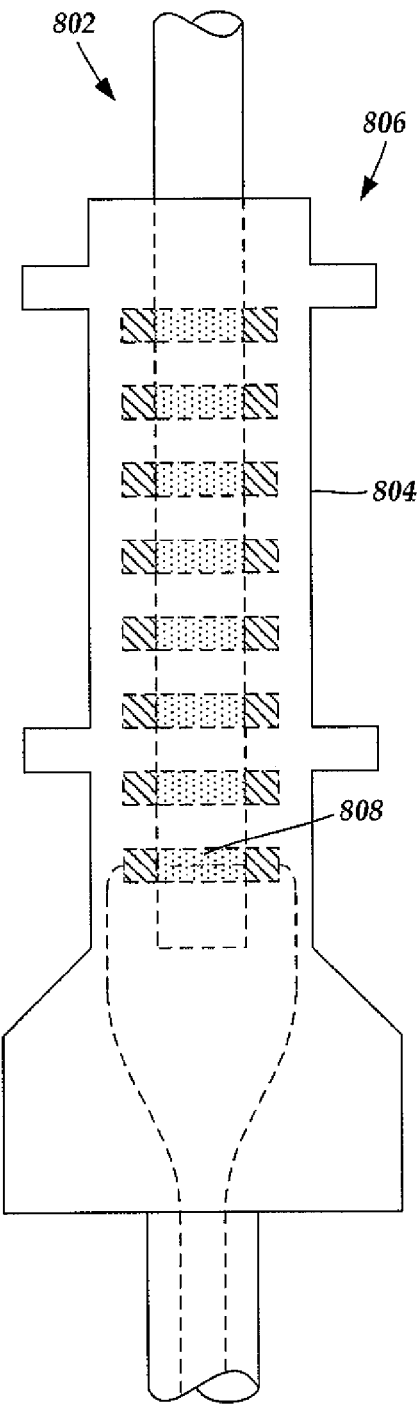
FIG. 8 is a schematic side view of one embodiment of a proximal end of a lead (or lead extension) inserted into a connector disposed on a distal end of a trial system cable, the lead (or lead extension) including a proximal-most terminal aligned with a single conductor pin disposed in the connector that is split into two separate conductor-pin portions, the proximal-most terminal electrically coupling the two conductor-pin portions to one another, according to the invention.

In at least some embodiments, a single conductor pin may be split into two electrically-isolated conductor-pin portions that are each independently electrically coupled to connective contacts (see e.g., 520 and 522 of FIG. 5A) disposed at a proximal end of the trial system cable. FIG. 8 is a schematic side view of one embodiment of a proximal end of a lead (or lead extension) 802 inserted into a connector 804 disposed on a distal end of a trial system cable 806. The connector 804 includes a proximal-most terminal 808 of the lead (or lead extension) 802 aligning with a single conductor pin 810 disposed in the connector 804 that is split into two electrically-isolated conductor-pin portions. In FIG. 8, the two conductor-pin portions of the conductor pin 810 are disposed laterally to one another, in a manner similar to the conductor pins (608 and 610 in FIGS. 6B-6C). In alternate embodiments, the two conductor-pin portions of the conductor pin 810 are disposed longitudinally to one another, in a manner similar the conductor pins (710 and 712 in FIG. 7). In at least some embodiments, splitting the conductor pin 810 into two conductor-pin portions may have an advantage of occupying less space than two complete conductor pins.

In at least some embodiments, the connection monitoring system 500 electrically couples with the proximal-most terminal of the inserted lead or lead extension, as shown in FIGS. 5C-8. In at least some embodiments, the connection monitoring system 500 electrically couples with other terminals besides the proximal-most terminal of the inserted lead or lead extension. In at least some embodiments, the connection monitoring system 500 electrically couples with a pair of terminals, as shown in FIGS. 5A-5B and 9A-10. In at least some embodiments, the connection monitoring system 500 electrically couples with more than two terminals. In at least some embodiments, the connection monitoring system 500 employs more than two conductor pins. In at least some embodiment, more than two conductor pins align with a single terminal. In at least some embodiments, more than two conductor pins align with a plurality of terminals.

In at least some embodiments, the connection monitoring system 500 is configured and arranged to determine where a disconnection occurs in an implantable medical lead system 502. For example, in at least some embodiments the connection monitoring system 500 differentiates between a disconnection occurring between the lead (or lead extension) 504 and the trial system cable 506 from a disconnection occurring between the trial system cable 506 and the external trial system 508 (or the trial system cable extension 534), or between the trial system cable extension 534 and the external trial system 508.

In at least some embodiments, the connection monitoring system 500 may recognize a plurality of non-overlapping impedance ranges for the implantable medical lead system 502. In at least some embodiments, detection of impedance within a first range may indicate a loss of connectivity at a first location and a detection of impedance within a second range may indicate a loss of connectivity at a second location.

Figure 9A:
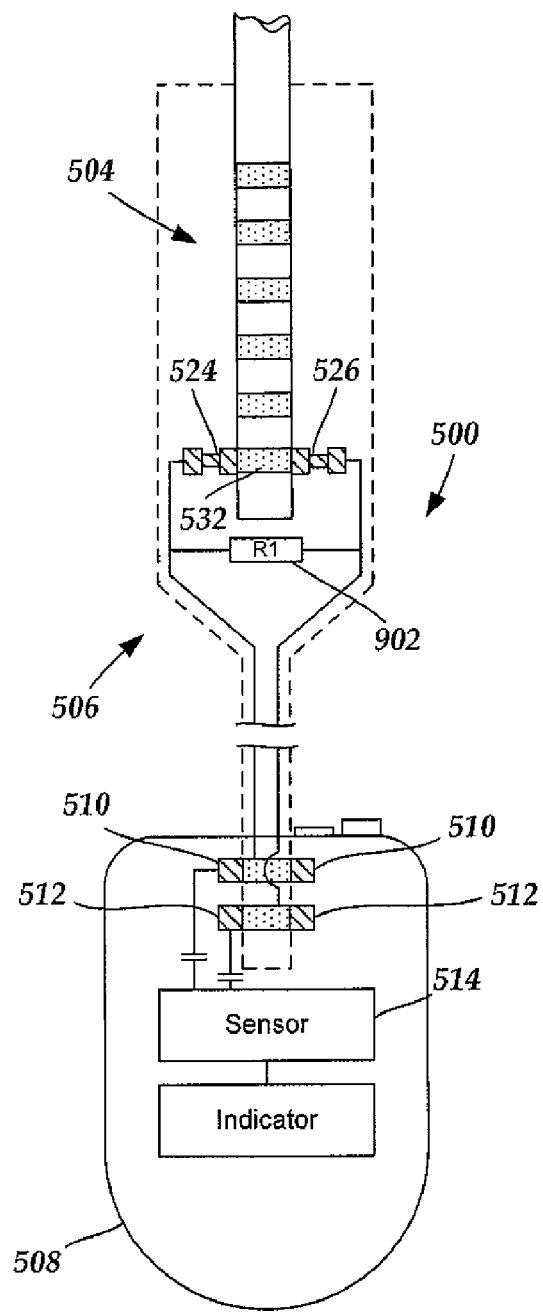
FIG. 9A is a schematic view of one embodiment of a connection monitoring system for an implantable medical lead system, the connection monitoring system including a conductive path that includes a resistor in parallel with a terminal and flanking conductor pins, according to the invention.

In at least some alternate embodiments, one or more resistors may be placed in a conductive path parallel with conductor pins disposed on a distal end of a trial system cable 506. In FIG. 9A, the connection monitoring system 500 includes a resistor "R1" 902 in parallel with conductor pins 524 and 526. Consequently, when the trial system cable 506 is improperly inserted into the external trial system 508, the sensor 514 may indicate that impedance is within a first impedance range. In at least some embodiments, the first impedance range has an infinite impedance, or impedance within a relatively high range, because conductor pins 510 and 512 are not electrically coupled to one another. When the trial system cable 506 is properly inserted into the external trial system 508, and the lead (or lead extension) 504 is improperly inserted into the trial system cable 506, the sensor 514 may indicate impedance that is within a second impedance range. In at least some embodiments, the second impedance range is approximately equal to resistor R1. When the lead (or lead extension) 504 is properly inserted into the trial system cable 506, and the trial system cable 506 is properly inserted into the external trial system 508, then the sensor 514 may indicate impedance that is within a third impedance range that is not infinite and does not overlap with the first impedance range. In at least some embodiments, the third impedance range is lower than the second impedance range.

Figure 9B:
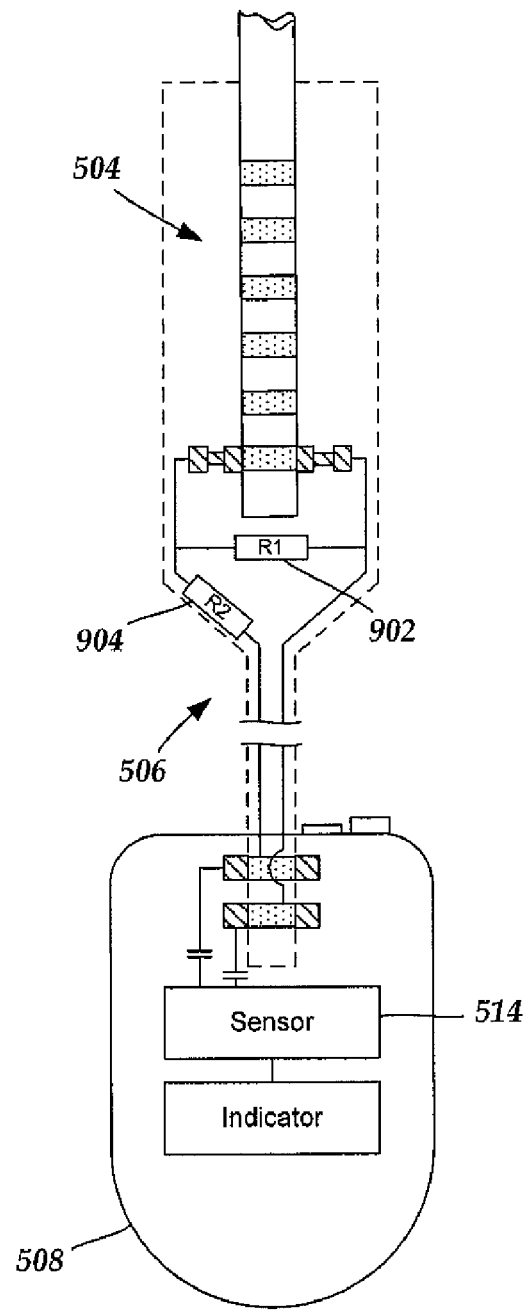
FIG. 9B is a schematic view of one embodiment of a connection monitoring system for an implantable medical lead system, the connection monitoring system including a conductive path that includes a first resistor in parallel with a terminal and flanking conductor pins and a second resistor in series with the first resistor and the terminal with flanking conductor pins, according to the invention.

Alternately, in at least some embodiments, one or more additional resistors may be placed in a conductive path in series with R1. In FIG. 9B, resistor "R2" 904 is shown in series with resistor R1 902. When resistors R2 904 and R1 902 are in series, as shown in FIG. 9B, the first impedance range is still infinite when the trial system cable 506 is not properly inserted to the external trial system 508. When the trial system cable 506 is properly inserted into the external trial system 508, but the lead 504 is improperly inserted into the trial system cable 506, the second impedance range is approximately equal to R1+R2. When the trial system cable 506 is properly inserted into the external trial system 508 and the lead 504 is properly inserted into the trial system cable 506, the third impedance range is approximately equal to R2. In at least some embodiments, one or more additional resistors may be disposed on the trial system cable extension (534 in FIG. 5B), thereby providing a unique fourth impedance range when there is a loss of connectivity involving the trial system cable extension (534 in FIG. 5B).

In at least some embodiments, the connection monitoring system can be used to distinguish which port of a multi-port external trial system a disconnection occurs. Any suitable number of ports may be employed to receive trial system cables or trial system cable extensions including, for example, one, two, three, four, five, six, seven, eight, nine, ten, eleven, twelve, or more ports. In at least some embodiments, each port may include a unique connection monitoring system, such as the connection monitoring system 500 shown in FIGS. 5A-5C. In other embodiments, a single connection monitoring system may be used to monitor the electrical connectivity between components of an implantable medical lead system disposed within a first port, and also monitor the electrical connectivity between components of the same implantable medical lead system or of a different implantable medical lead system disposed within a second port. In at least some embodiments, the connection monitoring system may also be used to monitor the electrical connectivity between components of the same implantable medical lead system or additional implantable medical lead systems disposed in additional ports of the external trial system. In at least some embodiments, the connection monitoring system may also be used to distinguish the type of device disposed in one or more ports of the external trial system.

Figure 10:
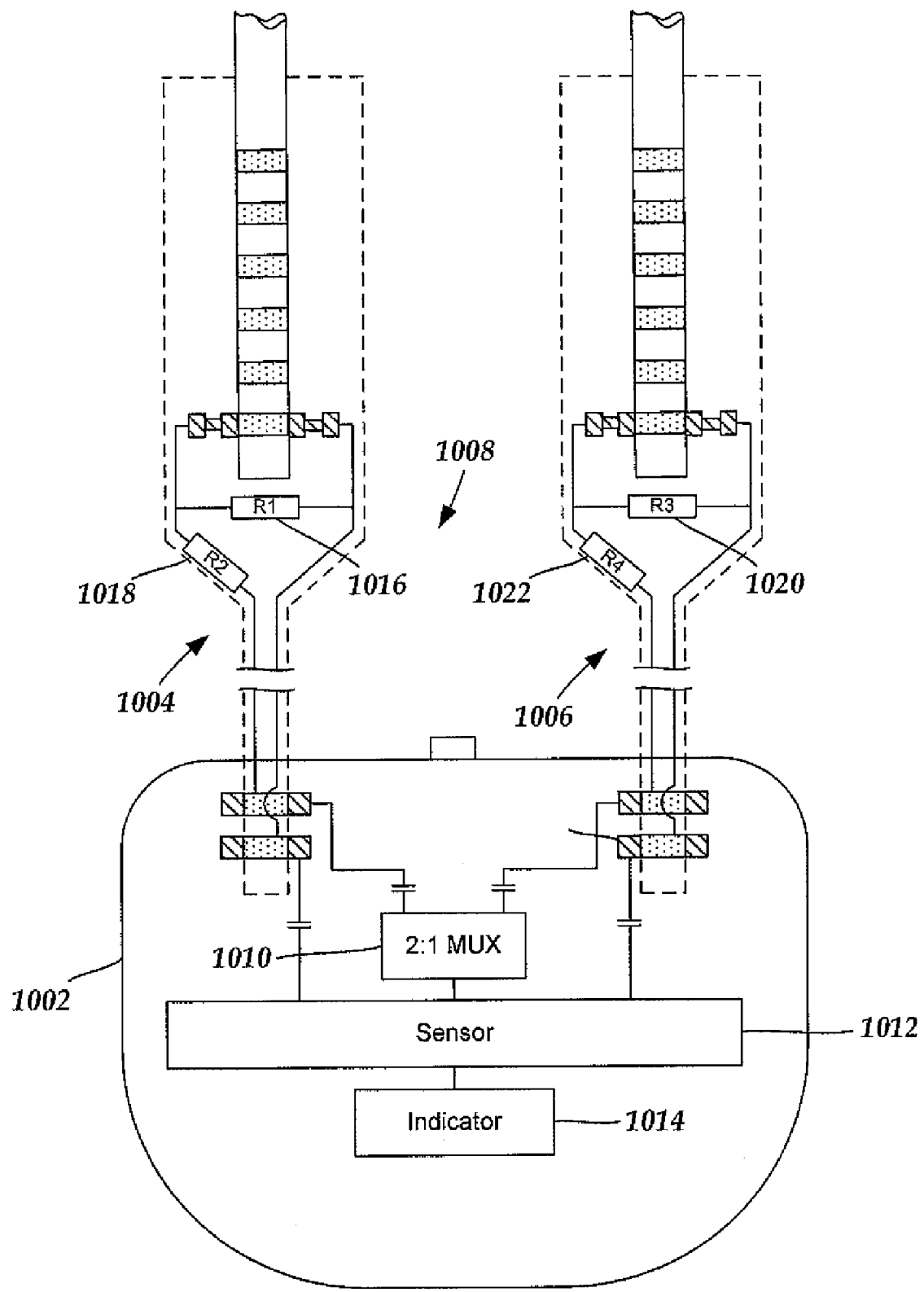
FIG. 10 is a schematic view of one embodiment of a connection monitoring system for an implantable medical lead system, the implantable medical lead system having an external trial system with multiple ports and the connection monitoring system including a multiplexer configured and arranged for monitoring the connectivity between the leads and trial system cables inserted into each port, according to the invention.

In FIG. 10, an external trial system 1002 is shown that is configured and arranged to receive two trial system cables 1004 and 1006. A connection monitoring system 1008 includes a conductive path with a 2:1 multiplexer 1010 electrically coupled to both trial system cables 1004 and 1006. In at least some embodiments, the 2:1 multiplexer 1010 alternates back-and-forth between the electrically coupled trial system cables 1004 and 1006, thereby alternating the connection monitoring system 1008 between monitoring the connectivity of components electrically coupled to the trial system cable 1004 and monitoring the connectivity of components electrically coupled to the trial system cable 1006. In at least some embodiments, a loss of connectivity within either of the electrically coupled trial system cables 1004 and 1006 may be sensed by a sensor 1012 and signaled by an indicator 1014. In at least some embodiments, the sensor 1012 determines on which of the electrically coupled trial system cables 1004 and 1006 the loss of connectivity occurred. In at least some embodiments, the resistances of the resistors R1 1016 and R2 1018 disposed on the trial system cable 1004, either separately or in combination, are not equal to the resistances of the resistors R3 1020 and R4 1022 disposed on the trial system cable 1006, either separately or in combination. Thus, unique non-overlapping impedance ranges sensed by the sensor 1012 may correspond to both a particular trial system cable 1004 or 1006 and to particular loss-of-connectivity locations within each trial system cable 1004 and 1006. In at least some embodiments, the unique non-overlapping impedance ranges sensed by the sensor 1012 may correspond to one or more other types of accessory devices, such as a test load box or a connector box, which may also be disposed in one or more ports. In at least some embodiments, the one or more types of accessory devices each include at least one interface contact for electrically coupling with the external trial system 1002. Accordingly, the non-overlapping impedance ranges may be used to distinguish between different types of trial system cables and other devices which may be disposed in the external trial system 1002.

In at least some embodiments, the indicator may provide a different signal to correspond to the location of a loss of connectivity. For example, a beeping of a first frequency may indicate a loss of connectivity within the implantable medical lead system employing the trial system cable 1004 and a beeping of a second frequency may indicate a loss of connectivity within the implantable medical lead system employing the trial system cable 1006. Moreover, one beep may indicate a loss of connectivity between a lead (or lead extension) and the trial system cable 1004 or 1006 (depending on the frequency) and two beeps may indicate a loss of connectivity between the trial system cable 1004 or 1006 (depending on the frequency) and the external trial system 1002. In at least some embodiments, the indicator may form a message on a display indicating a loss of electrical connectivity. In at least some embodiments, the indicator may form a message on the display indicating where the loss of electrical connectivity occurred.

Figure 11:
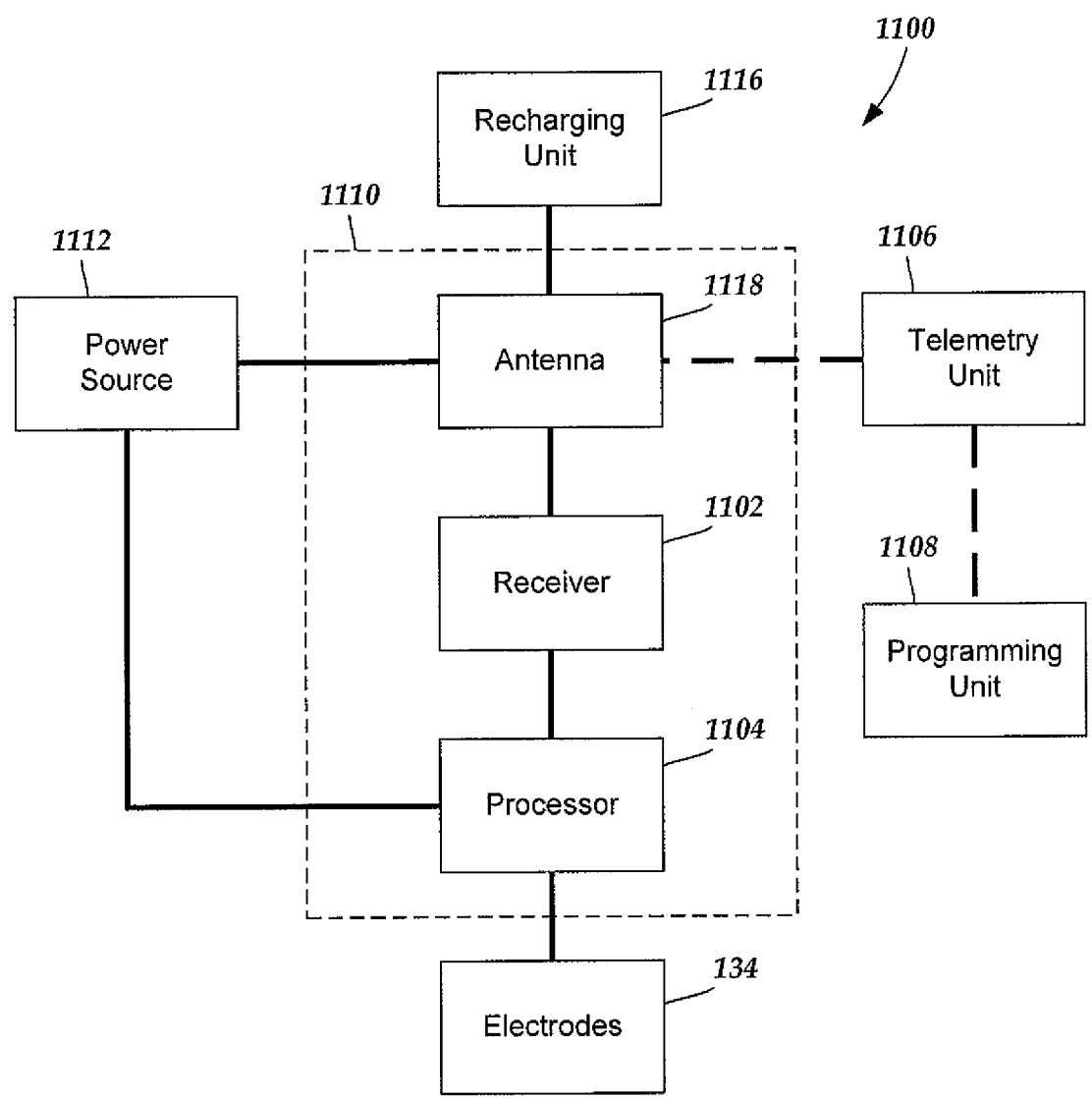
FIG. 11 is a schematic overview of one embodiment of components of an implantable medical lead system, including an electronic subassembly disposed within a control module, according to the invention.

FIG. 11 is a schematic overview of one embodiment of components of an implantable medical lead system 1100 including an electronic subassembly 1110 disposed within a control module. It will be understood that the implantable medical lead system can include more, fewer, or different components and can have a variety of different configurations including those configurations disclosed in the stimulator references cited herein.

Some of the components (for example, power source 1112, antenna 1118, receiver 1102, and processor 1104) of the implantable medical lead system can be positioned on one or more circuit boards or similar carriers within a sealed housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the paddle or lead body to stimulate nerve fibers, muscle fibers, or other body tissues near the implantable medical lead system. A processor 1104 is generally included to control the timing and electrical characteristics of the implantable medical lead system. For example, the processor 1104 can, if desired, control one or more of the timing, frequency, strength, duration, and waveform of the pulses. In addition, the processor 1104 can select which electrodes can be used to provide stimulation (or recording), if desired. In some embodiments, the processor 1104 may select which electrode(s) are cathodes and which electrode(s) are anodes. In some embodiments, the processor 1104 may be used to identify which electrodes provide the most useful stimulation (or recording) of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by a programming unit 1108. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the implantable medical lead system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and receiver 1102 can be used to modify or otherwise direct the operation of the implantable medical lead system. For example, the signals may be used to modify the pulses of the implantable medical lead system such as modifying one or more of pulse duration, pulse frequency, pulse waveform, and pulse strength. The signals may also direct the implantable medical lead system 1100 to cease operation, to start operation, to start charging the battery, or to stop charging the battery. In other embodiments, the implantable medical lead system 1100 does not include an antenna 1118 or receiver 1102 and the processor 1104 operates as programmed.

Optionally, the implantable medical lead system 1100 may include a transmitter (not shown) coupled to the processor 1104 and the antenna 1118 for transmitting signals back to the telemetry unit 1106 or another unit capable of receiving the signals. For example, the implantable medical lead system 1100 may transmit signals indicating whether the implantable medical lead system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A connection monitoring system for an implantable medical lead system, the connection monitoring system comprising:
   an implantable lead with a distal end and at least one proximal end, the lead comprising a plurality of terminals disposed at each proximal end;
   a first trial system cable having a distal end and at least one proximal end, the distal end of the first trial system cable configured and arranged to electrically couple with the lead, the first trial system cable comprising
      a first trial system cable connector disposed at the distal end of the first trial system cable, the first trial system cable connector having a longitudinal length, the first trial system cable connector configured and arranged to receive at least one of the proximal ends of the lead, and
      a pair of conductor pins disposed in the first trial system cable connector, the pair of conductor pins comprising a first conductor pin and a second conductor pin electrically isolated from one another, the pair of conductor pins are configured and arranged to become electrically coupled to one another when the lead is fully inserted into the first trial system cable connector with a first terminal of the plurality of terminals of the lead physically abutting each of the first conductor pin and the second conductor pin, wherein the first conductor pin and the second conductor pin are configured and arranged to remain electrically isolated from one another when the lead is not fully inserted into the first trial system cable connector;

an external trial system configured and arranged to electrically couple with the first trial system cable, wherein the external trial system is configured and arranged to electrically connect with the lead when the lead is electrically coupled to the first trial system cable and the first trial system cable is electrically coupled to the external trial system; and a sensor electrically coupled to the external trial system, the sensor configured and arranged for detecting a loss of electrical connectivity between the external trial system and the lead when the lead becomes electrically decoupled from the external trial system, wherein the sensor is electrically coupled to the first conductor pin and the second conductor pin.

2. The connection monitoring system of claim 1, further comprising a lead extension, the lead extension configured and arranged to electrically couple the implantable lead to the trial system cable.

3. The connection monitoring system of claim 1, further comprising an indicator electrically coupled to the sensor, the indicator configured and arranged for providing at least one signal when the sensor detects a loss of electrical coupling between the external trial system and the lead.

4. The connection monitoring system of claim 3, wherein the indicator is configured and arranged to emit at least one of an audio signal, a visual signal, a tactile signal, an olfactory signal, or a telemetry signal to a remote electronic device.

5. The connection monitoring system of claim 1, wherein the first conductor pin and the second conductor pin align with one another along the longitudinal length of the first trial system cable connector.

6. The connection monitoring system of claim 1, wherein the first conductor pin and the second conductor pin are longitudinally offset from one another along the longitudinal length of the first trial system cable connector.

7. The connection monitoring system of claim 1, wherein the first terminal is the proximal-most terminal of the plurality of terminals disposed on the lead.

8. The connection monitoring system of claim 1, further comprising additional conductor pins disposed in the first trial system cable connector, at least one of the additional conductor pins configured and arranged for aligning with a second terminal of the plurality of terminals when the lead is fully inserted into the first trial system cable.

9. The connection monitoring system of claim 1, wherein the first trial system cable further comprises
 a first connective contact disposed at the proximal end of the first trial system cable;
 a second connective contact disposed at the proximal end of the first trial system cable;
 at least one first conductor electrically coupling the first conductor pin to the first connective contact; and
 at least one second conductor electrically coupling the second conductor pin to the second connective contact.

10. The connection monitoring system of claim 9, wherein the external trial system further comprises an external trial system connector, the external trial system connector comprising a first conductor pin and a second conductor pin, the first conductor pin configured and arranged to electrically couple with the first connective contact of the first trial system cable and the second conductor pin configured and arranged to electrically couple with the second connective contact of the first trial system cable when the first trial system cable is fully inserted into the external trial system connector.

11. The connection monitoring system of claim 1, wherein the sensor is configured and arranged to detect a loss of electrical coupling between the external trial system and the lead by detecting impedance between the first conductor pin and the second conductor pin of the first trial system cable, the impedance being
 within a first impedance range when the first trial system cable is not fully inserted into the external trial system connector,
 within a second impedance range when the first trial system cable is fully inserted into the external trial system connector and the lead is not fully inserted into the first trial system cable connector, the second impedance range not overlapping the first impedance range, and
 within a third impedance range when the first trial system cable is fully inserted into the external trial system connector and the lead is fully inserted into the first trial system cable connector, the third impedance range not overlapping the first impedance range or the second impedance range.

12. The connection monitoring system of claim 1, further comprising a trial system cable extension electrically coupling the first trial system cable to the external trial system.

13. The connection monitoring system of claim 1, further comprising a second trial system cable, the second trial system cable having a distal end and at least one proximal end, the distal end of the second trial system cable configured and arranged to electrically couple with the lead and the at least one proximal end configured and arranged to electrically couple with the external trial system.

14. The connection monitoring system of claim 13, wherein the sensor is configured and arranged to distinguish between the first trial system cable and the second trial system cable based, at least in part, on a difference in impedance between the first trial system cable and the second trial system cable.

15. The connection monitoring system of claim 13, wherein the external trial system further comprises a multiplexer having a first input, a second input, and an output, wherein the first input of the multiplexer is electrically coupled to the first trial system cable and the second input of the multiplexer is electrically coupled to the second trial system cable, and wherein the output of the multiplexer is electrically coupled to the sensor.

16. The connection monitoring system of claim 1, further comprising an accessory device configured and arranged to electrically couple with the external trial system.

17. The connection monitoring system of claim 16, wherein the sensor is configured and arranged to distinguish between the first trial system cable and the accessory device based, at least in part, on a difference in impedance between the first trial system cable and the accessory device.

18. The connection monitoring system of claim 1, wherein the implantable medical lead system is an implantable electrical stimulation system.

19. The connection monitoring system of claim 1, wherein the implantable medical lead system is an implantable electrical recording system.

20. The connection monitoring system of claim 1, wherein the sensor is electrically coupled to the first conductor pin and the second conductor pin of the external trial system connector.

21. The connection monitoring system of claim 20, wherein the sensor is configured and arranged to detect a loss of electrical coupling between the external trial system and the lead by detecting impedance between the first conductor pin and the second conductor pin of the external trial stimulator.

22. A connection monitoring system for an implantable medical lead system, the connection monitoring system comprising:
- an implantable lead with a distal end and at least one proximal end, the lead comprising a plurality of terminals disposed at each proximal end;
- a lead extension having a distal end and at least one proximal end, the distal end of the lead extension configured and arranged to electrically couple with the lead, the lead extension comprising
    - a lead extension connector disposed at the distal end of the lead extension, the lead extension connector having a longitudinal length, the lead extension connector configured and arranged to receive at least one of the proximal ends of the lead, and
    - a pair of conductor pins disposed in the lead extension connector, the pair of conductor pins comprising a first conductor pin and a second conductor pin electrically isolated from the first conductor pin, the pair of conductor pins configured and arranged to become electrically coupled to one another when the lead is fully inserted into the lead extension connector with a first terminal of the plurality of terminals of the lead physically abutting each of the first conductor pin and the second conductor pin, wherein the first conductor pin and the second conductor pin are configured and arranged to remain electrically isolated from one another when the lead is not fully inserted into the lead extension connector;
- a control module configured and arranged to electrically couple with the lead extension, wherein the control module is configured and arranged to electrically connect with the lead when the lead is electrically coupled to the lead extension and the lead extension is electrically coupled to the control module; and
- a sensor electrically coupled to the external trial system, the sensor configured and arranged for detecting a loss of electrical connectivity between the control module and the lead when the lead becomes electrically decoupled from the control module, wherein the sensor is electrically coupled to the first conductor pin and the second conductor pin.

23. The connection monitoring system of claim 22, further comprising an indicator electrically coupled to the sensor, the indicator configured and arranged for providing at least one signal when the sensor detects a loss of electrical coupling between the control module and the lead.

* * * * *